United States Patent [19]

Kubota et al.

[11] Patent Number: 5,342,984
[45] Date of Patent: Aug. 30, 1994

[54] TRIORGANOMONOHALOGENOSILANE

[75] Inventors: Tohru Kubota; Mikio Endo, both of Niigata, Japan

[73] Assignee: Shin-Etsu Chemical Co., Ltd., Tokyo, Japan

[21] Appl. No.: 83,288

[22] Filed: Jun. 29, 1993

[30] Foreign Application Priority Data

Jul. 3, 1992 [JP] Japan .................. 4-176527

[51] Int. Cl.$^5$ ............................... C07F 7/08
[52] U.S. Cl. ........................ 556/477; 556/465
[58] Field of Search ................. 556/465, 477

[56] References Cited

U.S. PATENT DOCUMENTS

| | | | |
|---|---|---|---|
| 2,286,763 | 6/1942 | Rochow | 556/465 |
| 3,231,333 | 1/1966 | Jenkner et al. | 23/204 |
| 3,567,754 | 3/1971 | Alsgaard | 556/465 |
| 4,680,365 | 7/1987 | Muller et al. | 556/477 X |
| 4,780,556 | 10/1988 | Hata et al. | 556/477 X |
| 5,136,074 | 8/1992 | Shirahata | 556/465 X |
| 5,153,343 | 10/1992 | Shirahata | 556/465 |

OTHER PUBLICATIONS

Bazant et al., Organosilicon Compounds, vol. 2, Part, 1, Academic Press, N.Y. (1965).
European Search Report, EP-A-O 205-932 (Wacker-Chemie GmbH EP 93 11 0615 published Dec. 30, 1986.
Zhurnal OBschei Khim 11, vol. 55, No. 7, Jul. 1985, pp. 1520-1523 "Reaction of Allyl and Propargyl Chlorides with Hydrosilanes".

*Primary Examiner*—Paul F. Shaver
*Attorney, Agent, or Firm*—Sughrue, Mion, Zinn, Macpeak & Seas

[57] ABSTRACT

A triorganomonohalogenosilane is prepared by reacting a triorganomonohydrosilane represented by the following general formula (I):

$$R^1_3SiH \qquad (I)$$

with a halogenated allyl compound represented by the following general formula (II):

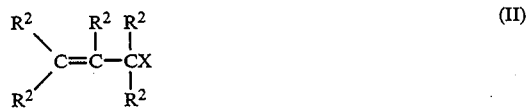

(II)

in the presence of metal palladium, or a salt or complex of palladium to replace the hydrogen atom directly bonded to the silicon atom of the triorganomonohydrosilane with a halogen atom. In Formula (I), the substituents $R^1$'s directly bonded to the silicon atom may be identical to or different from one another and each represents a monovalent organic group. In Formula (II), the substituents $R^2$'s may likewise be identical to or different from one another and each represents a hydrogen atom or a monovalent alkyl group and X represents a chlorine atom, a bromine atom or an iodine atom.

6 Claims, No Drawings

TRIORGANOMONOHALOGENOSILANE

Background of the Invention

The present invention relates to a monohalogenosilane which can be widely used as a silylating agent effective for the synthesis of medicines or the like or as a highly active starting material for preparing organosilicon compounds or compounds carrying organosilicon-containing groups as well as a method for preparing the monohalogenosilane.

As methods for preparing triorganomonohalogenosilane compounds, there have conventionally been known those comprising reacting triorganomonohydrosilanes with a molecular halogen per se such as a molecular chlorine or bromine so that hydrogen atoms directly bonded to silicon atoms are directly substituted with halogen atoms. Such methods are disclosed in, for instance, J. Org. Chem., 1950, 15, p. 552. These methods require the use of a harmful molecular halogen per se such as a molecular chlorine or bromine and a problem of safety supervision correspondingly arises. In addition, C—H bonds which constitute a part of the structure of a triorganomonohydrosilane compound simultaneously take part in the halogen-substitution reaction when the molecular halogen comes in contact with the triorganomonohydrosilane compound. For this reason, the reaction accompanies the formation of undesirable by-products and this results in substantial reduction of practical yield of the intended compound, i.e., triorganomonohalogenosilane.

ZH. Obshch. Khimo, 1974, 44, p. 2439 discloses another method for substitution which has been developed for the elimination of the problem of safety. In this method, halogenated allyls which are not expensive and can easily be handled are used as halogen sources instead of a molecular halogen per se such as a molecular chlorine or bromine which becomes a cause of the problem concerning safety. More specifically, a halogenated allyl is reacted with a triorganomonohydrosilane in the presence of a platinum catalyst. In this reaction, the triorganomonohydrosilane undergoes an addition reaction with the halogenated allyl to give a large quantity of halogenopropylsilane as a by-product and this likewise results in substantial reduction in the yield of the intended product.

SUMMARY OF THE INVENTION

Accordingly, an object of the present invention is, in general, to solve the foregoing problems associated with the conventional techniques for preparing triorganomonohalogenosilane and more specifically to provide a method for preparing the same, which is highly safe and can provide the silane in a high yield as well as the products prepared according to the foregoing method.

The foregoing object of the present invention can effectively be accomplished by providing a method for preparing a triorganomonohalogenosilane which comprises the step of reacting a triorganomonohydrosilane represented by the following general formula (I):

$$R^1_3SiH \quad (I)$$

with a halogenated allyl compound represented by the following general formula (II):

in the presence of metal palladium, or a salt or complex of palladium to replace the hydrogen atom directly bonded to the silicon atom of the triorganomonohydrosilane with a halogen atom.

In Formula (I), the substituents $R^1$'s directly bonded to silicon atom may be identical to or different from one another and each represents a monovalent organic group. In Formula (II), the substituents $R^2$'s may likewise be identical to or different from one another and each represents a hydrogen atom or a monovalent alkyl group. X represents a chlorine atom, a bromine atom or an iodine atom.

The method for preparing the monohalogenosilane compound according to the present invention is highly safe since the method does not require the use of a highly harmful substance such as a halogen gas. In the method of the present invention, by-products are formed in only small amounts and the method ensures the production of the intended product in a high yield. Moreover, the method of the invention permits the production of the intended monohalogenosilane compound in a high purity since it does not require the use of any reaction solvent at all and thus the method can industrially effectively be practiced.

DETAILED EXPLANATION OF THE INVENTION

In the method for preparing a monohalogenosilane compound according to the present invention, examples of the monovalent organic group of the triorganomonohydrosilane which is reacted with the halogenated allyl compound include hydrocarbon groups such as alkyl groups, alkenyl groups, alkynyl groups and aryl groups. In addition to these groups, the monovalent organic group may be, for instance, hydrocarbon groups having substituents such as halogenated alkyl groups and halogenated aryl groups.

Specific examples of such triorganomonohydrosilanes silanes are ethyldimethylsilane, triethylsilane, methyldi-n-propylsilane, isopropyldimethylsilane, triisopropylsilane, t-butyldimethylsilane, t-butyldiphenylsilane, n-decyldimethylsilane, dimethylphenylsilane, 3-bromo-propyldimethylsilane, 4-chlorophenyldimethylsilane and tris(4-fluorophenyl)silane.

On the other hand, specific examples of the halogenated allyl compounds represented by the foregoing general formula (II) include allyl chloride, methallyl chloride, 3-chloro-1-butene, 1-chloro-3-pentene, allyl bromide, methallyl bromide and allyl iodide.

The reaction of the triorganomonohydrosilane with the halogenated allyl compound is carried out in the presence of a palladium catalyst. The palladium catalyst used in this reaction may be metal palladium. The palladium catalyst may be, in addition to metal palladium, palladium salts such as palladium chloride, palladium acetate, palladium propionate and bisacetylacetonatopalladium; and palladium complexes such as dichlorobisbenzonitrile palladium, dichlorobisacetonitrile palladium, dichlorobistriphenylphosphine palladium and tetrakistriphenylphosphine palladium.

If metal palladium is used as a catalyst, it is preferably used in the form of powder because of its high surface area and, in particular, the metal palladium is used in the form of an active carbon- or alumina-supported palladium catalyst since it can easily be handled.

In principle, this reaction does not require the use of any reaction solvent, but aprotic reaction solvents such as tetrahydrofuran, toluene and decalin may be used in the reaction.

The amount of the halogenated allyl compound reacted with the triorganomonohydrosilane preferably ranges from 1 to 2 times the equivalent amount of the latter. On the other hand, the amount of the catalyst used in the reaction ranges from 1 to 10000 ppm and preferably 10 to 1000 ppm on the basis of the amount of the triorganomonohydrosilane.

The reaction is carried out at a temperature preferably ranging from 40 to 150° C. It is recommendable that the reaction be carried out in a reaction apparatus such as a reactor equipped with, for instance, a stirring machine, a thermometer, a reflux condenser and a dropping funnel.

Specifically, the foregoing reaction permits the preparation of, for instance, monochlorosilane compounds such as ethyldimethylchlorosilane, triethylchlorosilane, methyldi-n-propylchlorosilane, isopropyldimethylchlorosilane, triisopropylchlorosilane, t-butyldimethylchlorosilane, t-butyldiphenylchlorosilane, n-decyldimethylchlorosilane, dimethylphenylchlorosilane and 4-chlorophenyldimethylchlorosilane; monobromosilane compounds such as triethylbromosilane, t-butyldimethylbromosilane, 3-bromopropyldimethylbromosilane and tris(4-fluorophenyl)bromosilane; and monoiodosilane compounds such as triethyliodosilane and t-butyldimethyliodosilane.

In general, the products formed through the aforementioned reaction can be represented by the following general formula:

$$R^1{}_3SiX$$

wherein X represents a chlorine, bromine or iodine atom.

The yield of the foregoing reaction is substantially higher than that achieved by the conventional methods and is, in general, equal to approximately 100%.

The present invention will hereinafter be explained in more detail with reference to the following working Examples, but the present invention is by no means limited to these specific Examples.

Example 1

To a 500 ml glass flask equipped with a stirring machine, a thermometer, a reflux condenser and a dropping funnel, there were added 108.7 g (1.2 mole) of methallyl chloride and 0.03 g of palladium acetate, the temperature of the mixture was raised up to 60 to 70° C., then 116.3 g (1.0 mole) of triethylsilane was dropwise added to the mixture over 2 hours through the dropping funnel to carry out the reaction of the methallyl chloride and triethylsilane and thereafter the reaction mixture was aged at 100° C. for one hour.

The reaction solution obtained after the aging was distilled to give a distillate having a boiling point range of from 144 to 145° C. Thus, 147.7 g of triethylchlorosilane having a purity of 99.9% was obtained. The yield thereof was found to be 98.0%.

Example 2

The same procedures used in Example 1 were repeated except that 0.5 g of 10% palladium-carbon was substituted for 0.03 g of the palladium acetate used in Example 1. A distillate having a boiling point range of from 144 to 145° C. was fractionated through distillation and thus 144.1 g of triethylchlorosilane having a purity of 99.8% was obtained. The yield thereof was found to be 95.6%.

Example 3

The same procedures used in Example 1 were repeated except that 0.05 g of dichlorobisbenzonitrile palladium was substituted for 0.03 g of the palladium acetate used in Example 1. A distillate having a boiling point range of from 144 to 145° C. was recovered through distillation and thus 147.3 g of triethylchlorosilane having a purity of 99.9% was obtained. The yield thereof was found to be 97.7%.

Example 4

The same procedures used in Example 1 were repeated except that 0.05 g of bisacetylacetonatopalladium was substituted for 0.03 g of the palladium acetate used in Example 1. A distillate having a boiling point range of from 144 to 145° C. was fractionated through distillation and thus 146.3 g of triethylchlorosilane having a purity of 99.9% was obtained. The yield thereof was found to be 97.1%.

Example 5

The same procedures used in Example 1 were repeated except that 145.2 g (1.2 mole) of allyl bromide was substituted for 108.7 g of the methallyl chloride used in Example 1 to perform the reaction of the allyl bromide with the triethylsilane. A distillate having a boiling point range of from 162 to 164° was fractionated through distillation and thus 185.0 g of triethylbromosilane having a purity of 99.4% was obtained. The yield thereof was found to be 94.8%.

Example 6

The same procedures used in Example 1 were repeated except that 201.6 g (1.2 mole) of allyl iodide was substituted for 108.7 g of the methallyl chloride used in Example 1 to perform the reaction of the allyl iodide with the triethylsilane. A distillate having a boiling point range of from 191 to 193° C. was fractionated through distillation and thus 226.4 g of triethyliodosilane having a purity of 98.3% was obtained. The yield thereof was found to be 93.5%.

Example 7

To a 500 ml glass flask equipped with a stirring machine, a thermometer, a reflux condenser and a dropping funnel, there were added 135.8 g (1.5 mole) of methallyl chloride and 0.05 g of palladium acetate, the temperature of the mixture was raised up to 60 to 70° C., then 116.3 g (1.0 mole) of t-butyldimethylsilane was dropwise added to the mixture over 3 hours through the dropping funnel to carry out the reaction of the methallyl chloride and the t-butyldimethylsilane and the reaction mixture was aged at 100° C. for 2 hours. The reaction solution obtained after the aging was distilled to give a distillate having a boiling point range of from 124 to 126° C. Thus, 145.9 g of t-butyldimethylchlorosilane having a purity of 99.8% was obtained. The yield of the product was found to be 96.8%.

Example 8

The same procedures used in Example 7 were repeated except that 1.0 g of 10% palladium-carbon was substituted for 0.05 g of the palladium acetate used in Example 7. A distillate having a boiling point range of from 124 to 126° C. was recovered through distillation and thus 143.9 g of t-butyldimethylchlorosilane having a purity of 99.6% was obtained. The yield of the product was found to be 95.5%.

Example 9

The same procedures used in Example 7 were repeated except that 181.5 g (1.5 mole) of allyl bromide was substituted for 135.8 g of the methallyl chloride used in Example 7 to perform the reaction of the allyl bromide with the t-butyldimethylsilane. A distillate having a boiling point range of from 143 to 145° C. was fractionated through distillation and thus 185.8 g of t-butyldimethylbromosilane having a purity of 99.5% was obtained. The yield of the product was found to be 95.2%.

Example 10

To a 500 ml glass flask equipped with a stirring machine, a thermometer, a reflux condenser and a dropping funnel, there were added 91.8 g (1.2 mole) of allyl chloride and 0.03 g of palladium acetate, the temperature of the mixture was raised up to 40 to 45° C., then 136.3 g (1.0 mole) of dimethylphenylsilane was dropwise added to the mixture over 3 hours through the dropping funnel to carry out the reaction of the allyl chloride and the dimethylphenylsilane and the reaction mixture was aged at 50° C. for 3 hours. The reaction solution obtained after the aging was distilled to give a distillate having a boiling point range of from 80 to 84° C./16 mmHg. Thus, 163.9 g of dimethylphenylchlorosilane having a purity of 99.9% was obtained. The yield of the product was found to be 96.0%.

Example 11

The same procedures used in Example 10 were repeated except that 170.7 g (1.0 mole) of p-chlorophenyldimethylsilane was substituted for 136.3 g of the dimethylphenylsilane used in Example 10 to carry out the reaction of the allyl chloride and the p-chlorophenyldimethylsilane. A distillate having a boiling point range of from 103 to 104° C./11 mmHg was recovered through distillation and thus 197.1 g of p-chlorophenyldimethylchlorosilane having a purity of 99.5% was obtained. The yield of the product was found to be 96.1%.

The foregoing results clearly indicate that the reaction of a triorganomonohydrosilane with a halogenated allyl compound in the presence of a palladium catalyst can provide, with ease, a highly pure triorganomonohalogenosilane in a high yield without accompanying the formation of any by-product in a significant amount.

What is claimed is:

1. A method for preparing a triorganomonohalogenosilane comprising the step of reacting a triorganomonohydrosilane represented by the following general formula (I):

$$R^1{}_3SiH \qquad (I)$$

(wherein the substituents $R^1$'s may be identical to or different from one another and each represents a monovalent organic group with a hologenated allyl compound represented by the following general formula (II):

$$\begin{array}{c} R^2 \\ \diagdown \\ \diagup \\ R^2 \end{array} C=C-CX \begin{array}{c} R^2 \; R^2 \\ | \; | \\ | \; | \\ R^2 \end{array} \qquad (II)$$

wherein the substituents $R^2$'s may be identical to or different from one another and each represents a hydrogen atom or a monovalent alkyl group and X represents a chlorine, bromine or iodine atom in the presence of metal palladium, or a salt or complex of palladium to replace the hydrogen atom directly bonded to the silicon atom of the triorganomonohydrosilane with a halogen atom.

2. The method for preparing a triorganomonohalogenosilane as set forth in claim 1 wherein the triorganomonohydrosilane is at least one silane compound selected from triethylsilane and t-butyldimethylsilane.

3. The method for preparing a triorganomonohalogenosilane as set forth in claim 1 wherein the palladium compound is metal palladium; a palladium salt selected from the group consisting of palladium chloride, palladium acetate, palladium propionate and bisacetylacetonatopalladium; or a palladium complex selected from the group consisting of dichlorobisbenzonitrile palladium, dichlorobisacetonitrile palladium, dichlorobistriphenylphosphine palladium and tetrakistriphenylphosphine palladium.

4. The method for preparing a triorganomonochlorosilane as set forth in claim 1 wherein the halogenated allyl compound is at least one compound selected from allyl chloride and methallyl chloride.

5. The method for preparing a triorganomonobromosilane as set forth in claim 1 wherein the halogenated allyl compound is allyl bromide.

6. The method for preparing a triorganomonoiodosilane as set forth in claim 1 wherein the halogenated allyl compound is allyl iodide.

* * * * *

UNITED STATES PATENT AND TRADEMARK OFFICE
CERTIFICATE OF CORRECTION

PATENT NO. : 5,342,984
DATED : August 30, 1994
INVENTOR(S) : Tohru Kubota and Mikio Endo It is certified that error appears in the above-identified patent and that said Letters Patent is hereby corrected as shown below:

Column 6, line 14, delete "hologenated" and insert
--halogenated--.

Signed and Sealed this

Twenty-ninth Day of November, 1994

Attest:

BRUCE LEHMAN

Attesting Officer     Commissioner of Patents and Trademarks